United States Patent [19]

Straub et al.

[11] Patent Number: 5,250,691

[45] Date of Patent: Oct. 5, 1993

[54] HETEROARYL DERIVATIVES OF MONOCYCLIC BETA-LACTAM ANTIBIOTICS

[75] Inventors: Henner Straub, Regensburg; Jakob-Matthias Drossard, Tegernheim, both of Fed. Rep. of Germany

[73] Assignee: E. R. Squibb & Sons, Inc., Princeton, N.J.

[21] Appl. No.: 756,939

[22] Filed: Sep. 9, 1991

[51] Int. Cl.$^5$ .................... A61K 31/495; C07D 417/14
[52] U.S. Cl. ........................ 544/355; 546/14; 546/17; 546/156; 544/235; 544/237; 544/353; 544/354
[58] Field of Search ........................ 540/355

[56] References Cited

U.S. PATENT DOCUMENTS

| | | | |
|---|---|---|---|
| 3,978,064 | 8/1976 | Johnson et al. | 260/287 K |
| 4,217,453 | 8/1980 | Christensen et al. | 544/373 |
| 4,224,336 | 9/1980 | Christensen et al. | 424/274 |
| 4,587,047 | 5/1986 | Breuer et al. | 260/239 A |
| 4,610,824 | 9/1986 | Truner | 540/355 |
| 4,670,553 | 6/1987 | Breuer et al. | 540/363 |
| 4,743,685 | 5/1988 | Breuer et al. | 540/363 |
| 4,772,693 | 9/1988 | Breuer | 540/363 |
| 4,775,670 | 10/1988 | Sykes et al. | 514/210 |
| 4,904,775 | 2/1990 | Sundeen et al. | 540/363 |

FOREIGN PATENT DOCUMENTS

| | | |
|---|---|---|
| 0010426 | 10/1979 | European Pat. Off. |
| 0254495 | 7/1987 | European Pat. Off. |
| 0304158 | 7/1988 | European Pat. Off. |
| 0342423 | 11/1989 | European Pat. Off. |
| 0343574 | 11/1989 | European Pat. Off. |
| 0420069 | 4/1991 | European Pat. Off. |
| 0484881 | 5/1992 | European Pat. Off. |

OTHER PUBLICATIONS

Mochida, et al.; Aminothiazolylglycyl Derivatives of Carbacephem Antibiotics, Feb. 1987, pp. 182-189, Journal of Antibiotics.

Mochida, et al.; Aminothiazolylglycol Derivatives of Carbacephems, Jan. 1987, pp. 14-21, Journal of Antibiotics.

*Primary Examiner*—Mark L. Berch
*Attorney, Agent, or Firm*—Ellen K. Park

[57] ABSTRACT

Compounds having the formula

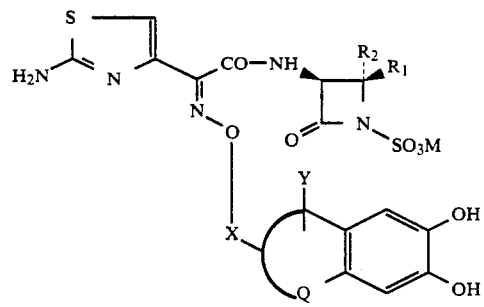

exhibiting antibacterial activity.

14 Claims, No Drawings

HETEROARYL DERIVATIVES OF MONOCYCLIC BETA-LACTAM ANTIBIOTICS

FIELD OF THE INVENTION

This invention relates to antibacterial agents and, in particular, to β-lactams.

BRIEF DESCRIPTION OF THE INVENTION

Compounds having the formula

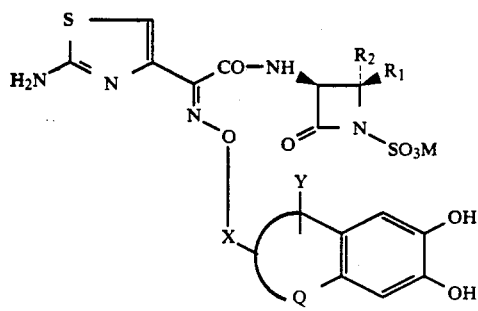

and pharmaceutically acceptable salts thereof exhibit antibacterial activity. In formula 1, and throughout the specification, the symbols are as defined below:

$R_1$ and $R_2$ are the same or different and each is hydrogen, alkyl, alkenyl, alkynyl, cycloalkyl, phenyl, substituted phenyl or a 4, 5, 6 or 7-membered heterocycle (hereinafter referred to as $R_a$), or one of $R_1$ and $R_2$ is hydrogen and the other is azido, halomethyl, dihalomethyl, trihalomethyl, alkoxycarbonyl, phenylethyl, 2-phenylethenyl, 2-phenylethynyl, carboxyl, —$CH_2X_1$ [wherein $X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

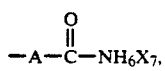

—$S$—$X_2$, or —$O$—$X_2$ wherein A, $X_2$, $X_6$ and $X_7$ are as hereinafter defined], —$S$—$X_2$ or —$O$—$X_2$ [wherein $X_2$, is alkyl, substituted alkyl, phenyl, substituted phenyl, phenylalkyl, (substituted phenyl) alkyl, formyl, alkanoyl, substituted alkanoyl, phenylalkanoyl, substituted phenylalkanoyl, phenylcarbonyl, substituted phenylcarbonyl, heteroaryl, heteroarylalkyl, heteroarylalkanoyl or heteroarylcarbonyl, and in the case of when $X_1$ is O—$X_2$ then $X_2$ can also be alkylideneamino, alkanoylamino, carboxyalkylideneamino, alkylsulphonylamino, alkoxycarbonyl, alkylsulphonylamino or N,N-cyclodialkanoylamino]. In addition $R_1$ and $R_2$ can be

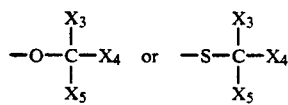

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, substituted phenylcarbonyl, phenylalkylcarbonyl, substituted phenylalkylcarbonyl, carboxyl, alkoxycarbonyl, aminocarbonyl, substituted aminocarbonyl, or cyano] or

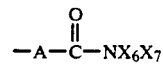

[wherein A is —CH=CH—, —$(CH_2)_m$—, —$(CH_2)_m$—O—, —$(CH_2)_m$—NH—, or —$CH_2$—S—$CH_2$—, m is 0, 1 or 2, and $X_6$ and $X_7$ are the same or different and each is hydrogen, alkyl, phenyl or substituted phenyl, or $X_6$ is hydrogen an $X_7$ is amino, substituted amino, alkanoylamino or alkoxy, or $X_6$ and $X_7$ when taken together with the nitrogen atom to which they are attached form a 4, 5, 6 or 7-membered heterocycle];

M is hydrogen, or a cation capable of forming a pharmaceutically acceptable salt. Preferred salts include sodium and potassium.

Q completes a 6-membered aromatic or nonaromatic heterocyclic ring, optionally substituted with an oxo, having 1 or 2 heteroatoms independently selected from N and $NR_{12}$;

$R_{12}$ is hydrogen, lower alkyl, cycloalkyl or carboxyalkyl, or a salt thereof;

X is attached through an available carbon atom and is $(CH_2)_n$ wherein n is 1, 2, 3 or 4 or $CR_3R_4$ wherein $R_3$ and $R_4$ are the same or different and each is hydrogen, $CH_3$ or $C_2H_5$ or $R_3$ and $R_4$ taken together with the carbon atom to which they are attached form a 3, 4, 5, 6 or 7-membered cycloalkyl ring;

Y is attached through an available carbon atom and is hydrogen, amino, hydroxy, halogen, carboxamide or carboxyl (provided that the heterocyclic ring is not quinoxaline).

Preferred compounds are when X is $CH_2$ and Q completes a quinoline ring, where Y is attached through an available carbon atom and is carboxyl or Q completes a quinolone ring, where Y is attached through an available carbon atom and is hydrogen and $R_{12}$ is carboxyalkyl. The compounds of this invention are pictured as acids or salts. They can also exist, however, as zwitterions (internal or inner salts), and these are also included within the language "pharmaceutically acceptable salts" and the scope of this invention.

DETAILED DESCRIPTION OF THE INVENTION

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "cycloalkyl" refers to cycloalkyl groups having 3, 4, 5, 6 or 7 carbon atoms.

The term "substituted alkyl" refers to alkyl groups substituted with one or more (preferably 1, 2 or 3) azido, amino (—$NH_2$), halogen, hydroxy, carboxy, cyano, alkoxycarbonyl, aminocarbonyl, alkanoyloxy, alkoxy, phenyloxy, (substituted phenyl)oxy, $R_a$-oxy, mercapto, alkylthio, phenylthio, (substituted phenyl) thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The term "substituted alkanoyl" refers to alkanoyl groups substituted with one or more (preferably 1, 2 or 3) azido, amino ($-NH_2$), halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups.

The term "substituted phenyl" refers to a phenyl group substituted with 1, 2 or 3 amino ($-NH_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_a$") refers to substituted and unsubstituted, aromatic and nonaromatic groups containing one or more (preferably 1, 2 or 3) nitrogen, oxygen or sulfur atoms. Exemplary substituents are oxo ($=O$), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

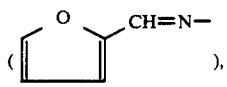

benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1, 2, 3-triazolyl, 1,2.4triazolyl, imidazolyl, thiazolyl, thiadiazolyl, pyrimidinyl, oxazolyl, triazinyl and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1imidazolidinyl, 3-benzyl-2-oxo-1-imidazolidinyl, 3 (2-aminoethyl)-2-oxo-1-imidazolidinyl, 3-amino2-oxo-1-imidazolidinyl, 3-[alkoxycarbonyl)amino]2-oxo-1-imidazolidinyl, 3-[2-[(alkoxycarbonyl)amino]-ethyl]-2-oxo-1-imidazolidinyl, 2-oxo-1pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula $-NX_8X_9$ wherein $X_8$ is hydrogen, alkyl, phenyl, substituted phenyl, phenylalkyl or (substituted phenyl)alkyl, and $X_9$ is alkyl, phenyl, substituted phenyl, phenylalkyl, (substituted phenyl)alkyl, hydroxy, cyano, alkoxy, phenylalkoxy or amino.

The β-lactams of formula 1 have activity against gram-negative organisms. Of particular interest is the good activity against gram negative organisms such as Pseudomonas in vitro and in vivo exhibited by the compounds of this invention. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

Compounds of formula 1 may be prepared by coupling a compound having the formula:

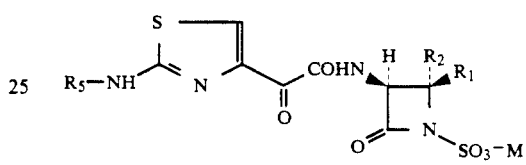

wherein $R_5$ is hydrogen or a suitable protecting group such as formyl or trityl with a compound of the formula:

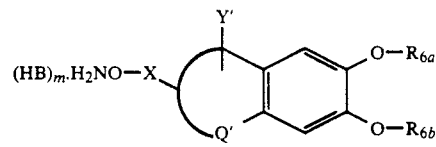

wherein $R_{6a}$ and $R_{6b}$ are independently hydrogen or a suitable phenol-protecting group or $R_{6a}$ and $R_{6b}$ together form a catechol protecting group such as Si(t-butyl)$_2$; Q' is defined as Q with the proviso that in the case where $R_{12}$ is carboxyalkyl (HOOC-alkyl) the carboxy group may also be protected by a suitable protecting group $R_{7a}$ ($R_{7a}$-OOC-alkyl) such as t-butyl, diphenylmethyl, allyl or trimethylsilylethyl, Y' is defined as Y with the proviso that in the case of Y is carboxy the carboxy group may also be protected by a suitable protecting group $R_{7a}$ ($R_{7b}$- OOC), wherein $R_{7b}$ is defined as $R_{7a}$, and HB is a mineral acid, sulfonic acid or another non-nucleophilic acid capable of forming a stable hydroxylamine salt and m is 0, 1, or 2 or fractions of 1 or 2. All synthesis of compounds using intermediates carrying protecting groups such as $R_5$, $R_{6a}$, $R_{6b}$, $R_{7a}$ and $R_{7b}$ in formulae 2, 3 and 6 provide protected derivatives of 1 which must be finally deprotected.

Alternatively, the compounds of formula 1 can be prepared by reacting a compound of the formula

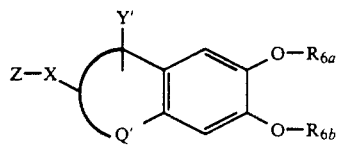

wherein Z is a leaving group such as halogen, trifluoroacetate, alkylsulfonate, arylsulfonate or other activated esters of alcohols; wherein X, Q', Y', R$_{6a}$ and R$_{6b}$ are the same as above with the proviso that if R$_5$ is trityl then R$_{6a}$ and R$_{6b}$ may also be benzyl or another protecting group which can be removed by catalytic hydrogenation; with a compound of the formula

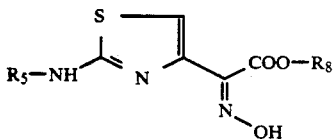

wherein R$_5$ is as defined above and R$_8$ is hydrogen or a carboxyl protecting group which can be removed under conditions wherein R$_{7a}$ and R$_{7b}$ remain inert. If R$_5$ is trityl then R$_8$ may also be p-nitrobenzyl to form a compound of the formula

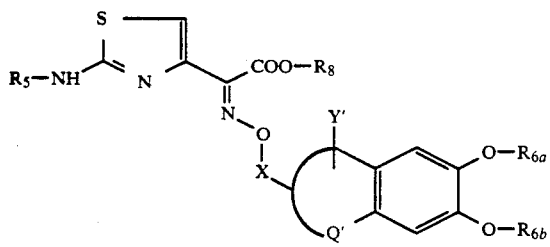

wherein R$_5$, R$_{6a}$, R$_{6b}$, R$_8$, Y' and Q' have hereinbefore been defined. Compound 6, wherein R$_8$ is hydrogen is then reacted with a compound of the formula

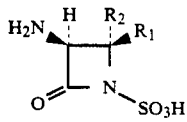

to form compounds of the invention represented by formula 1.

Alternatively, the compounds of formula 6 can also be prepared by reacting compound 3 with a compound of the formula

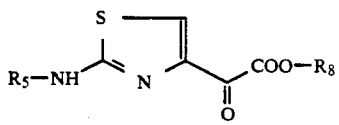

wherein R$_5$ and R$_8$ are as hereinbefore defined.

Compounds of formula 3 can be prepared by treatment of a N-protected derivative of a hydroxylamine of the formula

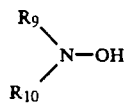

wherein R$_9$ and R$_{10}$ are combinations of suitable protecting groups such as hydrogen, t-butyloxycarbonyl, benzyloxy-carbonyl or R$_9$ and R$_{10}$ form a divalent cyclic protective group such as the isopropylidene [(CH$_3$)$_2$C=] or a phthalyl group with a compound of the formula 4, wherein Z is a leaving group as defined above, in an organic solvent and in the presence of a base such as triethylamine or an alkalimetal carbonate.

Alternatively, the alcohols of formula

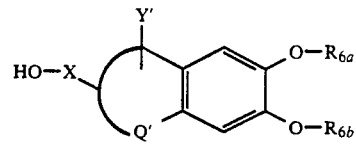

can be used instead of compounds of formula 4 for the above reaction with compounds of formula 9, provided the alcohols are preactivated under reaction conditions known in the art e.g. by using Mitsunobu conditions (triphenyl phosphine/diethyl azodicarboxylate/tetrahydrofuran). To provide the derivatives of formula 4 wherein Z is a leaving group, the alcohols of formula 10 were transformed in a separate step by using standard methodology.

The various combination of the protecting groups in compounds of formula 3 are not restricted by the specific protecting groups of the starting materials of formula 4, 9 or 10. Subsequent replacement of any protecting group in compounds of formula 3 by another protecting group by an additional deprotection-reprotection sequence is a preferred method to obtain specific derivatives such as persilylated derivatives of formula 3, wherein R$_{6a}$=R$_{6b}$=R$_{7b}$=Si(CH$_3$)$_3$ and m=O.

To provide a compound of formula

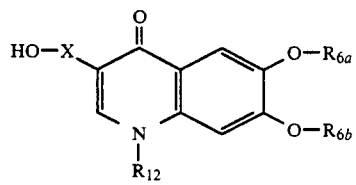

i.e. a compound of formula 10, wherein Y' is hydrogen and Q' completes a quinolone ring (incorporation of CO and NR$_{12}$) and R$_{12}$ is a lower alkyl, cycloalkyl or protected carboxyalkyl, a compound of formula 11

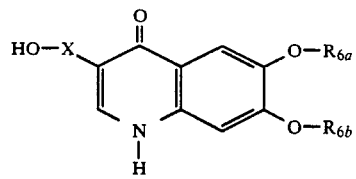

is alkylated with alkyl-, cycloalkyl- or substituted alkylhalogenide such as Cl—CH$_2$—COO—R$_{7a}$ in a solvent such as dimethylformamide and in the presence of a base such as potassium carbonate.

Compounds of formula 11 wherein X is CH$_2$, can be prepared by reduction of a compound of formula

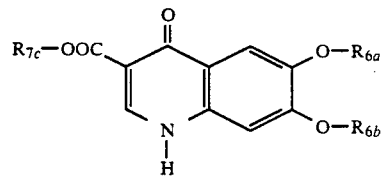

In addition to direct reduction of esters of formula 12, wherein $R_{7c}$ is a lower alkyl or another suitable protecting group, the esters of formula 12 can first be deprotected or hydrolyzed (e.g. with a base such as sodium hydroxide) and the so obtained acid of formula 12, wherein $R_{7c}$ is hydrogen, can be reduced thereafter with a complex hydride such as diborane in tetrahydrofuran to provide the desired compound of formula 11, wherein X is $CH_2$. Compounds of formula 12 are known from the literature (B. Riegel et al., J. Am. Chem. Soc. 68, 1946, p 1264).

Alternatively, an ester of formula 12 can be converted to an ester of formula

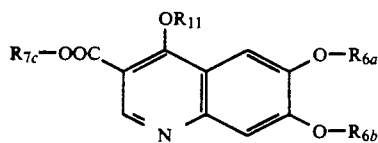

wherein $R_{11}$ is alkyl, arylalkyl or another suitable protecting group, as described in the literature (A. Weissberger and E. C. Taylors (Ed.) *The Chemistry of Heterocyclic Compounds*, Vol. 32, 391 pp. and 566 pp. 1977, John Wiley & Sons, London.)

Reduction of compounds of formula 13 with reducing agents such as lithium aluminum hydride provides an alcohol of formula

which is converted to the desired alcohol of formula 11, wherein $X=CH_2$, by removal of the protecting group $R_{11}$. Standard functional group interconversions of the esters of formula 13 or the alcohols of formula 14 can also provide the homolog or substituted alcohols of formula 15

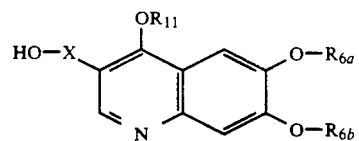

wherein X is $(CH_2)_n$ and n is 2, 3, 4 or X is $CR_3R_4$ and $R_3$ and $R_4$ are defined as above. Removal of the protecting group $R_{11}$ in compounds of formula 15 provides the quinolons of formula 11.

Analogously, a compound of formula 10b,

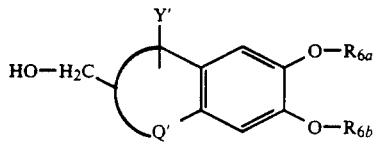

i.e. a compound of formula 10, wherein Y' is defined as hereinbefore, Q' completes a 6-membered saturated, unsaturated or aromatic heterocyclic ring optionally having up to 2N atoms and X is $CH_2$, can be prepared by reduction of corresponding compounds of formula 16,

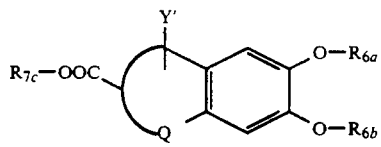

wherein $R_{7c}$ is hydrogen, lower alkyl or another suitable protecting group. In the presence of a protected carboxy group (Y'=COO—$R_{7b}$) a selective reduction is achieved by treatment of the free acid 16 ($R_{7c}$=H) with complex hydrides such as diborane whereas an ester 16 ($R_{7c}$ is a lower alkyl or another suitable protecting group) can also be reduced by suitable reducing agents such as lithium aluminum hydride provided Y' is defined as for Y (e.g. Y'=COOH).

Alternatively, compounds of formula 10c,

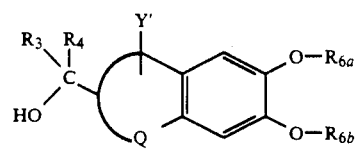

i.e. compounds of formula 10, wherein Y' is defined as hereinbefore, Q' completes a 6-membered aromatic heterocyclic ring optionally having up to 2N atoms and X is $CR_3R_4$ (as defined hereinbefore) with the proviso that X is attached to the heterocyclic ring in α-position to an N-ring atom, can be prepared by oxidation of a corresponding compound of formula 17

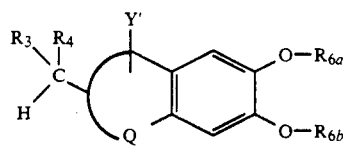

(Y', Q, $R_3$, $R_4$, $R_{6a}$ and $R_{6b}$ are as defined for the compound of formula 10c) to the corresponding N-oxide of formula 18

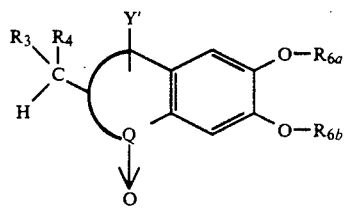

(Y', Q, $R_3$, $R_4$, $R_{6a}$ and $R_{6b}$ are as defined for the compound of formula 10c) and subsequent conversion with acetanhydride or trifluoro acetanhydride.

In addition, treatment of the N-oxide of formula 18 with acetyl chloride instead of acetanhydride provides the corresponding halogeno-compound of formula 19,

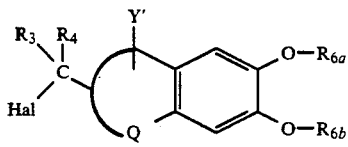

wherein the halogen is chloro (Y', Q, R$_3$, R$_4$, R$_{6a}$ and R$_{6b}$ are as defined for the compound of formula 10c). Such halocompounds can also be accessed by direct halogenation (e.g. N-bromosuccinimide) of a compound of formula 17. Starting from the alcohols 10b, 10c or the halogenides of formula 19 wherein R$_3$=R$_4$=hydrogen (X=CH$_2$) also the corresponding homolog derivatives of formula 10 wherein X is (CH$_2$)$_n$ and n is 2, 3, 4 can be prepared by functional group interconversion using standard methodology.

Standard functional group interconversion was also used to access compounds of formula 16 and 17 as exemplified for the preparation of the title compounds of Examples 2 and 3.

The compounds of formula 1 contain at least one chiral center—the carbon atom (in the 3-position of the β-lactam nucleus) to which the acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephalosporins (e.g., cephalosporin C).

The compounds of formula 1 have the imino substituent

and can, therefore, exist as the syn or anti isomer or as a mixture of isomers. All of these isomeric forms are within the scope of this invention. In general, however, the syn isomer of a compound of formula 1 has the greatest activity.

The following examples describe the manner and process of making and using the invention and are illustrative rather than limiting. It should be understood that there may be other embodiments which fall within the spirit and scope of the invention as defined by the claims appended hereto.

EXAMPLE 1

[2R-[2α, 3α(Z)]]-3-[[[[1-(2-Amino-4-thiazolyl-2-[(2-methyl-4-oxo-1-sulfo-3-azetidinyl)amino]-2oxoe-thylideneamino]oxy]methyl]-6,7-dihydroxy-4-oxo-1(4H)-quinolineacetic acid, disodium salt A.
1,4-Dihydro-4-oxo-6,7-bis(phenylmethoxy)-3-quinoline carboxylic acid 1. 1,2-Bis(phenylmethoxy)benzene To a solution of 1,2-dihydroxybenzene (60 g, 0.54 mol) in 240 mL acetone, potassium carbonate (220 g, 1.59 mol) was added. After heating to reflux, benzylbromide (256.6 g, 1.5 mol) was added dropwise. The mixture was heated to reflux overnight, cooled, and poured onto 1 liter ice-water. The resulting precipitate (title compound) was filtered off with suction, washed with water, and dried in vacuo.

20 Yield 143.50 g, (91.5%).
Melting point: 57–59° C.
1H-NMR (DMSO-d$_6$): δ5.11 (s,4H); 6.80–7.15 (m,4H); 7.25–7.60 (m,10H); ppm.

2. 3,4-Bis(phenylmethoxy)nitrobenzene

To a suspension of the title 1 compound (26 g, 89.5 mmol) in 120 mL acetic acid, 24 mL of 65% nitric acid in 120 mL acetic acid was added dropwise. From the resulting solution, the title compound crystallized on stirring. 50 mL acetic acid were added to improve stirring. After one hour, the mixture was poured onto 1 liter ice-water. The solid was filtered off with suction, washed with water, and recrystallized from 500 mL ethanol.

Yield: 27.15 g (90.5%).
Melting point: 95–97° C.
IR(KBr): 1350, 1510 cm$^{-1}$ (NO$_2$).
1H-NMR(DMSO-D$_6$): δ=5.26 (s,2H); 5.30 (s,2H); 7.20–7.60 (m,11H); 7.80–8.00 (m,2H); ppm.

3. 3,4-Bis(phenylmethoxy)benzeneamine

To a boiling solution of the title 2 compound (72.15 g, 215.2 mmol) in 1030 mL ethanol was added a hot solution of sodium sulfide nonahydrate (106.0 g, 430.4 mmol) in 140 mL water:ethanol (1:1,v/v). After the addition, the mixture was heated to reflux for 35 minutes and then cooled. The resulting precipitate (title compound) was filtered off, washed with water, and dried in vacuo.

Yield: 52.6 g (80%).
Melting point: 109–111° C.
IR(KBr): 3360, 3430 cm$^{-1}$ (NH$_2$).
1H-NMR(DMSO-D$_6$): δ=4.73 (s,broad,2H); 4.93 (s,2H); 5.04 (s,2H); 6.10 (dd,AB,1H); 6.38 (d,1H); 6.73 (d,AB,1H); 7.20–7.60 (m,10H); ppm.

4. [[[3,4-Bis(phenylmethoxy)phenyl]amino]-methylene]propanedioic acid

To a solution of the title 3 compound (52.6 g, 172.2 mmol) in 315 mL dimethylformamide, diethyl ethoxymethylenemalonate (42.8 g, 198.0 mmol) was added. After stirring for three days at room temperature, the solvent was distilled off in vacuo and the residue was triturated with water to give 86.7 g (quant.) of the title compound.

Melting point: 73–76° C.
IR(KBr): 1700 cm$^{-1}$ (CO). 1H-NMR(DMSO,D$_6$): δ=1.26, 1.27 (2t,6H); 4.13, 4.20 (2q,4H); 5.12 (s,2H); 5.18 (s,2H); 6.88 (dd,AB,1H); 7.06 (d,AB,1H); 7.22 (d,1H); 7.25–7.60 (m,10H); 8.32 (d,1H); 10.71 (d,1H); ppm.

5. 1,4-Dihydro-4-oxo-6,7-bis(phenyl-methoxy)-3-quinoline carboxylic acid, ethyl ester The compound of title 4 (2.55 g, 5.36 mmol) was added under stirring to 21 mL boiling diphenylether. The mixture was heated to reflux for 15 minutes while the resulting ethanol was distilled off. After cooling, ether was added to the resulting suspension. The precipitate (the title compound) was filtered off and dried in vacuo.

Yield: 160 g (70%).
Melting point: 291° C.
IR(KBr): 1795 cm$^{-1}$ (CO).
1H-NMR(TFA): δ=1.49 (s,3H); 4.61 (q,2H); 5.33 (s,4H); 7.20–7.50 (m,10H); 7.58 (s,1H); 7.98 (s,1H); 9.02 (s,1H); ppm.

6. 1,4-Dihydro-4-oxo-6,7-bis(phenylmethoxy)-3-quinoline carboxylic acid

To a solution of 9.0 g (0.16 mmol) potassium hydroxide in 240 mL ethanol (80%), 17.0 g (0.04 mmol) of the title 5 compound was added and the mixture was stirred at 80° C. for 20 hours. The solvent was removed in vacuo, and the residue was taken up in 300 mL water. The title compound was precipitated by slow addition of 2N hydrochloric acid, collected by suction, washed with water and ethanol, and dried in vacuo over phosphorus pentoxide.

Yield: 13.5 g (84%);
Melting point: 271-272° C. (dec.).

B.
3-(Hydroxymethyl)-6,7-bis(phenylmethoxy)-4(1H)-quinolinone

Under argon a 1M solution of boranetetrahydrofuran complex in tetrahydrofuran (400 mL) was added dropwise with stirring to the title A compound (32.0 g, 0.080 mol) at room temperature (evolution of hydrogen). After stirring at this temperature for an additional 40 minutes, the mixture was refluxed for 23 hours and then cooled to room temperature. After the slow addition of 2N sodium hydroxide (100 mL) at room temperature (evolution of hydrogen) stirring was continued for 2.5 hours. The precipitate was collected by suction and washed with tetrahydrofuran and ether to yield a crude material (31 g), which was suspended in water, collected by suction and dried in vacuo over phosphorus pentoxide.

Yield: 10.0 g (32%).

An additional crop of the title compound was obtained by evaporation of the mother liquors in vacuo and subsequent stirring of the residue with water-tetrahydrofuran (10:1) to form a precipitate, which was collected by suction, dried in vacuo over phosphorus pentoxide, suspended in ether, filtered and dried in vacuo over phosphorus pentoxide.

Yield: 9.0 g (29%).
Overall yield: 19.0 g (61%);
Melting point: 220° C. (sint) >280° C.
IR(KBr): 1622, 1602 cm$^{-1}$ $^1$H-NMR (DMSO-D$_6$): ∂=4.40 (d,2H;J=6Hz); 4.85 (t,1H;J=6Hz); 5.23 (s,2H); 5.28 (s,2H); 7.07 (s,1H); 7.2-7.6 (m,10H); 7.58 (s,1H); 7.76 (s,1H); 11.55 (s,broad,1H)ppm.

C.
3-(Hydroxymethyl)-4-oxo-6,7-bis(phenylmethoxy)-1(4H)-quinolineacetic acid, diphenylmethyl ester To a suspension of the title B compound (19.0 g, 49 mmol) in dry dimethylformamide (400 mL) potassium carbonate (9.0 g, 66 mmol) and diphenylmethyliodoacetate (20.8 g, 59 mmol) were added and stirring was continued for 15 hours at room temperature. The solvent was distilled off in vacuo and the residue was taken up in a mixture of ethyl acetate (350 mL) and water (100 mL). The organic layer was separated and washed with brine. After spontaneous crystallization from the organic layer, the title compound was collected by suction, washed with ethyl acetate and pentane, and dried in vacuo over phosphorus pentoxide.

Yield: 23.5 g (78%);
Melting point: 172-173° C.
IR(KBr): 1760, 1630, 1615 cm$^{-1}$
$^1$H-NMR (DMSO-d$_3$): ∂=4.42 (s,2H); 4.98 (s,2H); 5.02 (s,broad,1H); 5.24 (s,2H); 5.51 (s,2H); 6.95 (s,1H); 6.99 (s,1H); 7.2-7.6 (m,20H); 7.68 (s,1H); 7.88 (s,1H)ppm.

D.
3-[[(1,3-Dihydro-1,3-dioxo-2H-isoindol-2-yl)oxy]methyl]-4-oxo-6,7-bis(phenylmethoxy)-1(4H)-quinolineacetic acid, diphenylmethyl ester A solution of diethyl azodicarboxylate (6.6 g, 38 mmol) in dry tetrahydrofuran (50 mL) was dropped at 0° C. to a mixture of the title C compound (23.2 g, 38 mmol), triphenylphosphine (10.0 g, 38 mmol), N-hydroxyphtalimide (6.2 g, 38 mmol) in dry tetrahydrofuran (250 mL) and stirring was continued for 2.5 hours at 0°-5° C. and additional 12 hours at room temperature. The solvent was removed in vacuo and the residue was dissolved in a mixture of ethyl acetate (105 mL) and petroleum ether (45 mL). After standing overnight at 0° C., the precipitate was collected by suction, suspended in ethyl acetate (125 mL) for 15 minutes at room temperature, collected by suction, washed with few mL cold ethyl acetate and pentane and dried in vacuo over phosphorus pentoxide.

Yield: 15.3 g (53%);
Melting point: 177°-178° C.
IR(KBr): 1790, 1750, 1725, 1630 cm$^{-1}$
$^1$H-NMR (DMSO-D$_6$): ∂=4.98 (s,2H); 5.03 (s,2H); 5.20 (s,2H); 5.47 (s,2H); 6.81 (s,1H); 7.02 (s,1H); 7.2-7.6 (m,20H); 7.63 (s,1H); 7.80 (s,4H); 8.21 (s,1H)ppm.

E.
3-[(Aminooxy)methyl]-4-oxo-6,7-bis(phenylmethoxy)-1(4H)-quinolineacetic acid, diphenylmethyl ester A solution of methyl hydrazine (0.92 g, 20 mmol) in dichloromethane (75 mL) was dropped at −5° to 0° C. within 20 minutes into a solution of the title D compound (15.1 g, 20 mmol) in 150 mL dichloromethane. After stirring for additional 90 minutes at 0° to +3° C. the precipitate was filtered off (3.2 g) and the filtrate was evaporated in vacuo to leave a foam which solidified by stirring with a 1:1 mixture of ether and cyclohexane.

Yield: 12.2 g (97%);
Melting point: 137°-139° C.
IR(KBr): 1750, 1630 cm$^{-1}$
$^1$H-NMR (DMSO-d$_6$): ∂=3.5 (s,broad,2H); 4.48 (s,2H); 4.96 (s,2H); 5.21 (s,2H); 5.47 (s,2H); 6.85 (s,1H); 6.99 (s,1H); 7.2-7.5 (m,20H); 7.70 (s,1H); 7.98 (s,1H); ppm.

F(1). (Mono TEOC Compound)
4-Oxo-6,7-bis(phenylmethoxy)-3-[[[[[2-(trimethylsilyl)ethoxy]carbonyl]amino]oxy]methyl]-1-(4H)-quinolineacetic acid, diphenylmethyl ester

F(2) (Di-TEOC-Compound)
3-[[[Bis[[2-(trimethylsilyl)ethoxy]carbonyl]amino]oxy]oxy]methyl]-4-oxo-6,7-bis(phenylmethoxy)-1(4H)-quinolineacetic acid, diphenylmethyl ester A mixture of the title E compound (9.4 g; 15 mmol), triethylamine (1.5 g; 15 mmol) and 1-[2-(Trimethylsilyl)ethoxycarbonyloxy]benzotriazole (TEOC-OBT; 9.2 g; 33 mmol) in tetrahydrofurane (110 mL) was stirred at room temperature for 24 hours. TEOC-OBT was prepared according to literature procedures: R. G. Shute and D. H. Rich, *Synthesis*, 1987, 346. After removal of the solvent in vacuo the residue was taken up in ethyl acetate (140 mL) and water (50 mL) and the pH was adjusted to 2 by addition of 1N hydrochloric acid. The organic phase was separated, washed with 2N sodium hydroxide, water and brine, dried (calcium sulfate) and evaporated in vacuo to leave an oil (17 g) which was chromatographed on silica gel eluting with petroleum ether/ethyl acetate (gradient 3:7–1:9). Evaporation of the relevant fractions (32–57 and 119–145) yielded 4.5 g (33%) of the Di-TEOC compound F(2) (melting point=155°–156° C. from ether) and 5.8 g, 50% of the Mono-TEOC compound (melting point=70° C.) respectively.

F(1): IR(KBr): 1745 cm$^{-1}$
$^1$H-NMR(DMSO-d$_6$): δ=0.00 (s,9H); 0.91 (m,2H); 4.09 (m,2H); 4.15 (s,2H); 4.96 (s,2H); 5.20 (s,2H); 5.47 (s,2H); 6.85 (s,1H); 6.98 (s,1H); 7.15–7.50 (m,20H); 7.69 (s,1H); 8.01 (s,1H); 10.20 (s,1H)ppm.

F(2): IR(KBr): 1775, 1745 cm$^{-1}$
$^1$H-NMR (DMSO-d$_6$): δ=0.00 (s,18H); 0.85 (m,4H); 4.13 (m,4H); 4.82 (s,2H); 4.94 (s,2H); 5.20 (s,2H); 5.47 (s,2H); 6.86 (s,1H); 6.98 (s,1H); 7.15–7.50 (m,20H); 7.70 (s,1H); 8.02 (s,1H)ppm.

G.
3-[[Bis[[2-(trimethylsilyl)ethoxy]carbonyl]amino]oxy]-methyl]-6,7-dihydroxy-4-oxo-1(4H)-quinolineacetic acid N-Methyl-N-trimethylsilyl-trifluoroacetamide (MSFTA) (7.4 g; 37 mmol) was added to a solution of the title F (1) compound (8.5 g; 9.3 mmol) in N,N-dimethylformamide (DMF) (90 mL) and the resulting mixture was hydrogenated in the presence of palladium (10%) on charcoal (3.0 g). After 90 minutes the catalyst was filtered off and the filtrate was evaporated in vacuo. The residue was dissolved in methanol (40 mL), stirred for 20 minutes at room temperature, filtered again and the filtrate was evaporated in vacuo to leave a viscous oil which was solidified by stirring with few mL of a mixture of ether and petroleum ether. The crude precipitate (4.5 g; melting point 93°–97° C.) was purified by dissolving in dichloromethane (60 mL) and washing with water. After drying (calcium sulfate) and evaporation of the organic phase, the residue was stirred with petroleum ether (boiling point 40°–60° C.) for 5 hours, the precipitate was collected by suction and dried in vacuo.

Yield: 4.0 g (75%);
Melting point: 127° C. (dec).
This material still contained a trace of DMF (by $^1$H-NMR) but was used in the next step without any further purification.

IR(KBr): 1755 cm$^{-1}$
$^1$H-NMR (DMSO-d$_6$ TFA): δ=−0.05 (s,18H); 0.79 (m,4H); 4.08 (m,2H); 5.02 (s,2H); 5.32 (s,2H); 7.08 (s,1H); 7.70 (s,1H); 8.58 (s,1H) ppm.

H.
3-[(Aminooxy)methyl]-6,7-dihydroxy-4-oxo-1(4H)-quinolineacetic acid

With stirring, the title G compound (2.0 g; 35 mmol) was added in portions to trifluoroacetic acid (30 mL) at −10° C. and stirring was continued at −5° C. to 0° C. for additional 45 minutes. After removal of the excess of trifluoroacetic acid in vacuo, the residue was stirred with few mL dry ether for 30 minutes, the precipitate was collected by suction and dried in vacuo (1.6 g). Silylation of this salt (1.53 g; HI by HPLC=96.2%) by means of N-Methyl-N-trimethylsilyl-trifluoroacetamide (MSTFA) (4.35 mL, 22.5 mmol) in acetonitrile (40 mL) at room temperature for 30 minutes afforded, after evaporation in vacuo and stirring of the residue with isopropanol (30 mL), a precipitate which was collected by suction, washed with few mL dry methanol and dry ether and dried in vacuo.

Yield: 0.98 g (quant.); HI=91.9% (by HPLC).
IR(KBr): 1710, 1635 cm$^{-1}$
$^1$H-NMR (DMSO-d$_6$): δ=4.47 (s,2H); 4.90 (m,2H); 6.2 (s,broad,ca.5H); 6.70 (s,1H); 7.49 (s,1H); 7.48 (s,1H)ppm.

I.
(2R-cis)-3-[[(2-Formylamino-4-thiazolyl)oxoacetyl]amino]-2-methyl-4-oxo-1-azetidinesulfonic acid, monopotassium salt 1,8-Diazobicyclo[5.4.0]undec-7-ene (DBU) (16.5 ml; 0.11 mol) was dropped into a suspension of (2R-cis)-3-Amino-2-methyl-4-oxo-1-azetidinesulfonic acid, inner salt (18.02 g; 0.10 mol) in dry dichloromethane (180 mL) at 10° C. and stirring was continued at this temperature for an additional hour. Then the solution was cooled to −30° C. (solution A). Formylaminothiazolylglyoxylic acid (22.22 g; 0.111 mol) was suspended in dry dichloromethane (360 mL) and then dissolved by addition of triethylamine (17.0 mL; 0.122 mol). After being stirred for 1 additional hour insoluble material was filtered off and the filtrate was cooled to −30° C. (solution B).

Into solution B was added dropwise at −30° C. pyridine (0.62 mL) followed by trimethylacetyl chloride (13.38 g; 0.111 mol) and then by solution A. The mixture was stirred at −25° to −30° C. for 1 hour and then allowed to come to ambient temperature. After evaporation in vacuo the residue was taken up in ethanol (600 mL) and treated dropwise with a solution of potassium acetate (28 g; 0.285 mol) in ethanol (180 mL). After being stirred for 1 hour the precipitate was collected by suction, washed with ethanol, dried in vacuo and purified by recrystallization from hot water (270 mL).

Yield 28.4 g (70%);
Melting point: >230° C.;
IR (KBr) 1755, 1670 cm$^{-1}$
$^1$H-NMR (DMSO-d$_6$): δ=1.22 (d,3H); J=7 Hz); 4.07 (quin(ps), 1H; J=7 Hz; J'=6 Hz); 5.11 (dd,1H; J'=6 Hz; J''=8.5 Hz); 8.45 (s,1H); 8.56 (s,1H); 9.40 (d,1H;J''=8.5 Hz); 12.70 (s,1H) ppm.

J.
(2R-cis)-3-[[(2-Amino-4-thiazolyl)oxoacetyl]amino]-2-methyl-4-oxo-1-azetidinesulfonic acid The title I compound (20 g, 55.2 mmol) was suspended in 270 ml water. The pH was brought to 0.5 with 3N hydrochloric acid and the resulting solution was stirred for two days at room temperature. The precipitate was filtered off with suction, washed with water and dried in vacuo.

Yield: 12.6 g (68.4%).
Melting point: >300° C.
IR (KBr): 1710, 1760 cm$^{-1}$ (CO).
$^1$H-NMR (DMSO-d$_6$): δ=1.20 (d,3H), 4.03 (dq,1H), 5.02 (dd,1H), 8.19 (s,1H), 8.35 (s,broad,NH$_2$,SO$_3$H and water), 9.70 (d,1H) ppm.

K.
[2R-[2α,3α(Z)]]-3-[[[[1-(2-Amino-4-thiazolyl)-2-[(2-methyl-4-oxo-1-sulfo-3-azetidinyl)amino]-2-oxoethylidene]amino]oxymethyl-6,7-dihydroxy-4-oxo-1(4H)quinolineacetic acid, disodium salt Compound H (0.93 g; 2.4 mmol) was added in portions to a stirred solution of the Title J compound (0.69 g; 2.0 mmol) in N,N-dimethylformamide (60 mL) at room temperature and the pH of the solution was corrected to 2, by addition of 1N HCl. After being stirred at this pH for 48 hours the pH of the solution was raised to 6 by means of NaHCO$_3$-solution. The mixture was evaporated in vacuo to leave a brown solid (4.2 g) which was redissolved in water (10 mL), readjusted to pH=6.5 (sodium bicarbonate-solution), filtered and purified by MPLC on XAD-2 resin eluting with water containing raising amounts of acetonitrile (0% to 10%). Freeze-dried fractions having an HI=85-95% (by HPLC) were combined (0.86 g; 75%) and rechromatographed (MPLC) on XAD-2 resin eluting with water. Freeze-drying of the appropriate fractions afforded the desired monobactam as a colourless solid.

Yield: 300 mg (23%);
Melting point: 97° C. sint, >178° dec.;
HI=98% by HPLC;
IR(KBr): 1760 cm$^{-1}$
$^1$H-NMR (DMSO-d$_6$): δ=1.14 (d,3H;J=6 Hz); 3.95 (quintett,1H;J=6 Hz,J'=6 Hz); 4.43 (s,2H); 4.98 (s,2H); 5.08 (dd,J'=6 Hz,J''=8.5 Hz); 6.72 (s,1H); 6.90 (s,1H); 7.21 (s,broad,2H); 7.41 (s,1H); 7.71 (s,1H); 9.37 (d,1H,J''=8.5 Hz)ppm.

EXAMPLE 2

[2α,3α(Z)]]-2-[[[[1-(2-Amino-4-thiazolyl-2-[(2-methyl-4-oxo-1-sulfo-3-azetidinyl)amino]-2-oxoe-thylidene]amino]oxy]methyl]-6,7-dihydroxy-4-quinoline-carboxylic acid, disodium salt A.
2-[(Aminooxy)methyl-6,7-dihydroxy-4-quinoline-carboxylic acid, monohydrochloride 1. 2-Methyl-6,7-bis(phenylmethoxy)-4-quinolinecarboxylic acid A solution of the title 3 compound of Example 1 (5.0 g, 16.35 mmol) in dry ethanol (50 mL) was heated to reflux and a solution of pyruvic acid (2.28 mL, 32,7 mmol) in dry ethanol (10 mL) added dropwise. The mixture was stirred under reflux for four hours and cooled to room temperature. The precipitate was filtered off by suction, washed with acetone, and dried in vacuo.

Yield: 3.82 g (58%);
Melting point: 283° C. (dec.)

2. 2-Methyl-6,7-bis(phenylmethoxy)-4-quinolinecarboxylic acid, (phenylmethyl) ester To a suspension of the title 1 compound (10.0 g, 25 mmol) in dry dimethylformamide (300 mL) was added potassium carbonate (3.8 g, 27.5 mmol) and benzylbromide (3.3 mL, 27.5 mmol), and the mixture was stirred for one hour at 60° C. The reaction mixture was cooled to room temperature, poured into ice-water and extracted with ethyl acetate. The organic layer was separated, washed with brine, dried over sodium sulfate, and evaporated in vacuo. The residue was triturated with petroleum ether, filtered off by suction, and dried in vacuo.

Yield: 11.22 g (92%);
Melting point: 135° C.

3. 2-Methyl-6,7-bis(phenylmethoxy)-4-quinolinecarboxylic acid, (phenylmethyl) ester, 1-oxide To a solution of the title 2 compound (9.15 g, 18.69 mmol) in dry chloroform (150 mL) was added metachloroperbenzoic acid (11.73 g, 37.38 mmol), and the mixture was stirred overnight at room temperature. The solvent was removed in vacuo and the residue triturated with a mixture of saturated aqueous sodium bicarbonate-solution and ethyl acetate. The unsoluble material was filtered off by suction, washed with water, sodium bicarbonate-solution, and water and dried in vacuo.

Yield: 8.65 g (92%);
Melting point: 158° C.

4. 2-(Hydroxymethyl)-6,7-bis(phenylmethoxy)-4-quinolinecarboxylic acid, (phenylmethyl) ester A mixture of the title 3 compound (15.6 g, 30.86 mmol) and trifluoroacetic acid anhydride (TFAA) (75 mL) in dry chloroform (100 mL) was heated to reflux for four hours. The solvent and excess TFAA were evaporated in vacuo. The residue was triturated with a mixture of ethyl acetate and water and the crude compound filtered off by suction. Purification of this material was achieved by recrystallization from ethyl acetate.

Yield: 10.59 g (70%);
Melting point: 161° C.

5. t-Butyl-N-benzyloxycarbamate

To a stirred solution of O-benzylhydroxylamine (16.0 g, 0.13 mol) and di-t-butyldicarbonate (28.4 g, 0.13 mol) in a mixture of water (150 mL) and tetrahydrofuran (150 mL) 2N sodium hydroxide solution was added dropwise to adjust the pH to 8-9 and this pH was maintained for an additional two hours by occasional addition of 2N sodium hydroxide. After extraction with ethylacetate the combined organic layers were washed with brine, dried (Magnesium sulfate) and evaporated in vacuo to leave an oil which was used in the next step without any further purification. Yield 29 g (100%).

6. (Phenylmethoxy)imidodicarbonic acid, bis(1,1-dimethylethyl) ester

To a stirred solution of the title 5 compound (29 g, 0.13 mol) triethylamine (27.9 mL, 0.2 mol) and 4-dimethylamino-pyridine (trace) in dry tetrahydrofuran (200 mL) a solution of di-t-butyl dicarbonate (39.7 g, 0.18 mol) in 20 mL dry tetrahydrofuran was added dropwise at a rate that the temperature did not exceed 40° C. Stirring was continued at this temperature (40° C.) for additional 30 minutes and then at room temperature overnight. The mixture was taken up in ether, washed with buffer solution pH=4 (citrate) and brine, dried (magnesium sulfate) and evaporated in vacuo. From the oily residue (still containing few mL of ether) the title compound was crystallized by cooling to 0° C.

Melting point: 77.5°-78.5° C.
Yield 70.4%.

An analytical sample was recrystallized from petroleum ether (bp 40°-60° C.).
Melting point: 77.5°-78.5° C.
$C_{17}H_{25}NO_5$ % C calc. 63.14%, found 63.14% ; % H calc. 7.79%, found 7.82%; % N calc. 4.33%, found 4.35%.
IR(KBr): 1755 1730cm$^{-1}$;
$^1$H-NMR (DMSO-d$_6$) δ=1.49 (s, 18H); 4.88 (s, 2H), 7.42 (s, 5H) ppm.

7. Hydroxyimidodicarbonic acid, bis(1,1-dimethylethy)ester

A solution of the title 6 compound (8.09 g, 0.025 mol) in ethanol (150 mL) was hydrogenated in the presence of palladium (10%) on activated carbon (3.5 g). After 15 minutes the hydrogenation was completed (monitored by thin layer chromatography), the catalyst was removed by suction and the filtrate was evaporated in vacuo. The oily residue solidified by stirring with pentane.

Melting point 88.5°-89.5° C.
Yield 71.2%.

An analytical sample was recrystallized from petroleum ether (60°-70° C.).

Melting point sint 88.7° C., 91°-92° C.

$C_{10}H_{19}NO_5$ % C calc. 51.49%, found 51.48%; % H calc. 8.21%, found 8.21%; % N calc. 6.00%, found 6.02%.

IR(KBr): 1775 1752, 1685cm$^{-1}$ $^1$H-NMR (DMSO-d$_6$): δ=1.48 (s, 18H); 9.95 (s, 1H).

8. 2-[[[Bis[(1,1-dimethylethoxy)carbonyl]amino]oxy]methyl]-6,7-bis(phenylmethoxy)-4-quinolinecarboxylic acid, (phenylmethyl) ester To a suspension of the title 4 compound (6.6 g, 13.37 mmol), the title 7 compound (6.24 g, 26.74 mmol) and triphenylphosphine (4.32 g, 16.05 mmol) in tetrahydrofuran (500 mL) was added dropwise a solution of diethylazodicarboxylate (2.52 mL, 16.05 mmol) in tetrahydrofuran (100 mL). The mixture was stirred overnight at room temperature, and additional triphenylphosphine (1.08 g, 4.01 mmol) and diethylazodicarboxylate (0.63 mL, 4.01 mmol) were added to the solution. Stirring for additional two days at room temperature, followed by the evaporation of the solvent in vacuo afforded crude title compound which was recrystallized from isopropanol. The resulting crystals were filtered off by suction, triturated with petroleum ether, and dried in vacuo.

Yield: 9.75 g (quant.);

Melting point: 131° C.

9. 2-[[[Bis[(1,1-dimethylethoxy)carbonyl]amino]oxy]methyl]-6,7-dihydroxy-4-quinolinecarboxylic acid The title 8 compound (5.0 g, 7.05 mmol) was dissolved in dimethylformamide (200 mL), palladium on charcoal (10%) added (0.5 g), and hydrogen bubbled through this mixture. After six hours an additional amount of the catalyst (0.5 g) was added and the hydrogenation continued for another six hours. The catalyst was filtered off by suction over hyflo and the filtrate evaporated in vacuo. The residue was triturated with water, filtered off by suction, and dried in vacuo.

Yield: 2.85 g (90%);

Melting point: 159° C.

10. 2-[(Aminooxy)methyl]-6,7-dihydroxy-4-quinolinecarboxylic acid, monohydrochloride A solution of the title 9 compound (2.1 g, 4.66 mmol) in 1N-hydrochloric acid was stirred overnight at room temperature. Some unsoluble material was filtered off by suction and the filtrate evaporated in vacuo. The residue was triturated with ether, filtered off by suction, and dried in vacuo.

Yield: 1.31 g (98%);

Melting point: 184° C. (dec.)

B. [2R-[2α,3α(Z)]]-2-[[[[1-(2-Amino-4-thiazolyl-2-[(2-methyl-4-oxo-1-sulfo-3-azetidinyl)amino-2-oxoethylidene]amino]oxy]methyl]-6,7-dihydroxy-4-quinolinecarboxylic acid, disodium salt A suspension of the title J compound of Example 1 (0.82 g, 2.44 mmol) and the title A compound (1.4 g, 4.88 mmol) in water (60 mL) was adjusted to pH 2 (by the addition of 1N sodium hydroxide) and stirred overnight at room temperature. According to TLC only little product was formed. For this reason the unsoluble starting materials were filtered off by suction, dried in vacuo, dissolved in dimethylformamide (50 mL) and stirred overnight at room temperature. The solvent was evaporated in vacuo, the residue triturated with ether, and the crude compound suspended in water. The pH was adjusted to 6.5 by the addition of 2N sodium hydroxide, the solution filtered, and the filtrate purified by MPLC on XAD using water as eluent. The product-containing fractions were combined and further purified by a second MPLC on XAD (water).

Yield: 0.22 g (15%) H.I.=95.8%. 0.07 g (5%) H.I.=96.6%.

Total Yield: 0.29 g (20%)

Melting point: 162° C. (dec.)

IR (KBr): 1760 cm $^1$H-NMR (200 MHz, DMSO-d$_6$+TFA): δ=1.15 (d, 3H); 4.04 (m, 1H); 5.14 (d, 1H); 5.61 (s, 2H); 7.05 (s, 1H); 7.55 (s, 1H); 8.05 (s, 1H); 8.09 (s, 1H) ppm.

EXAMPLE 3

[2R-[2α,3α(Z)]]-4-[[[[1-(2-Amino-4-thiazolyl-2-[(2-methyl-4-oxo-1-sulfo-3-azetidinyl)amino]-2-oxoethylidene]amino]oxy]methyl]-6,7-dihydroxy-2-quinolinecarboxylic acid, disodium salt

A. 4-[(Aminooxy)methyl]-6,7-dihydroxy-2-quinolinecarboxylic acid, trifluoroacetate (1:1) salt

1. 2-Formyl-6,7-bis(phenylmethoxy)-4-quinolinecarboxylic acid, (phenylmethyl) ester The title 2 compound of Example 2 (13.0 g, 26.5 mmol) was dissolved in dioxane (300 mL) and seleniumdioxide (7.1 g, 63.7 mmol) and water (100 mL) added. The mixture was heated to reflux for five hours and the precipitated selenium filtered off by suction. To the filtrate was added again seleniumdioxide (7.1 g) and the mixture heated to reflux overnight. The precipitated selenium was filtered off by suction over Hyflo and the filtrate evaporated in vacuo. The residue was dissolved in ethylacetate, washed with water, and dried over sodium sulfate. The solvent was evaporated in vacuo and the residue triturated with petroleumether. The title compound was filtered off by suction and dried in vacuo.

Yield: 11.1 g (83%)

Melting point: 131°-134° C.

2. 6,7-Bis(phenylmethoxy)-2,4-quinolinedicarboxylic acid, 4-(phenylmethyl)ester To a solution of the title 1 compound (5.5 g, 11 mmol) in pyridine (100 mL) was added tetrabutylammoniumpermanganate (6.3 g, 17 mmol) and the mixture stirred for one hour at room temperature. Sulfurdioxide was bubbled through the suspension and the solvent evaporated in vacuo. The residue was triturated with water and the crude product filtered off by suction. This material was suspended in water and the pH adjusted to 1.0 by the addition of phosphoric acid. After stirring overnight the title compound was filtered off by suction, washed with water, and dried in vacuo.

Yield: 4.43 g (78%)

Melting point: 284°-286° C.

3. 4-(Hydroxymethyl)-6,7-bis(phenylmethoxy)-2-quinolinecarboxylic acid, monolithium salt To a suspension of the title 2 compound (4.4 g, 8.47 mmol) in dry tetrahydrofuran (100 mL) and dry methanol (1 mL) was added lithiumborohydride (8.5 mL of a 2M-solution in tetrahydrofuran) and the mixture stirred overnight at room temperature. Since the reduction was not complete (as monitored by TLC), an additional amount of lithiumborohydride (4.25 mL of the solution mentioned above) was added. After stirring for two hours at room temperature the solvents were evaporated in vacuo, and the residue was triturated with ether. The precipitate was filtered off by suction, triturated with boiling water, filtered off by suction and dried in vacuo.

Yield: 3.4 g (95%)

4. 4-(Hydroxymethyl)-6,7-bis(phenylmethoxy)-2-quinolinecarboxylic acid, (phenylmethyl) ester To a solution of the title 3 compound (10.2 g, 24 mmol) in dimethylformamide (100 mL) was added benzylbromide (4.1 g) and the mixture heated to 60° C. for 90 minutes. The batch was poured into ice-water and the resulting precipitate extracted with ethyl acetate. The organic layer was dried over sodium sulfate and the solvent evaporated in vacuo. The residue was triturated with ether and recrystallized from toluene.

Yield: 2.76 g (23%)
Melting point: 187°-189° C.

5. 4-[[Bis[(1,1-dimethylethoxy)carbonyl]amino]oxymethyl]-6,7-bis-(phenylmethoxy)-2-quinolinecarboxylic acid, (phenylmethyl) ester To a solution of the title 4 compound (6.6 g, 13 mmol) in dry tetrahydrofuran (200 mL) was added N,N-bis-(tert.butoxycarbonyl)hydroxylamine (6.1 g, 26 mmol), triphenylphosphine (4.2 g, 15.6 mmol) and diethylazodicarboxylate (2.7 g, 15.6 mmol), and the mixture was stirred overnight at room temperature. According to TLC, the reaction was not complete, and therefore another 1.1 g (6.5 mmol) of diethylazodicarboxylate and 1.75 g (6.5 mmol) of triphenylphosphine were added. The mixture was stirred over the weekend at room temperature and evaporated in vacuo. The residue was triturated with ether and the precipitate filtered off by suction to afford 5.4 g of the title compound. Evaporation of the ether and trituration of the residue with methanol afforded another 2.0 g of the title compound. The crude product was purified by recrystallization from cyclohexane/toluene.

Yield: 5.0 g (53%)
Melting point: 155°-158° C.

6. 4-[[[Bis[(1,1-dimethylethoxy)carbonyl]amino]oxy]methyl]-6,7-bis-(phenylmethoxy)-2-quinolinecarboxylic acid 30 To a solution of the title 5 compound (6.7 g, 9.3 mmol) in dry dimethylformamide (200 mL) was added palladium on charcoal (0.6 g) and hydrogen bubbled through the mixture for six hours. Since the reduction was not complete, the catalyst was filtered off by suction and replaced by fresh palladium on charcoal (0.6 g). The hydrogenation was continued for another eight hours after which the reaction was complete. The catalyst was filtered off by suction over Hyflo and the solvent evaporated in vacuo. The residue was triturated with petroleum ether, filtered off by suction, and dried in vacuo.

Yield: 3.75 g (99%)
Melting point: 95°-98° C.

7. 4-[(Aminooxy)methyl]-6,7-dihydroxy-2-quinolinecarboxylic acid, trifluoroacetate (1:1) salt The title 6 compound (3.7 g, 9 mmol) was triturated with 1N-hydrochloric acid (100 mL) for 32 hours at room temperature. Evaporation and trituration with ether afforded 2.05 g of the compound from which only one BOC-group was removed. 1.7 g (4.85 mmol) of this compound were heated with trifluoroacetic acid (20 mL) to 80° C. for three hours after which the deprotection was complete. The TFA was evaporated in vacuo and the residue triturated with ether. The precipitate was filtered off by suction and dried in vacuo.

Yield: 1.6 g (59%)
Melting point: dec. at 170°-175° C.

B. [2R-[2α,3α(Z)]]-4-[[[[1-(2-Amino-4-thiazolyl-2-[(2-methyl-4-oxo-1-sulfo-3-azetidinyl)amino]-2-oxoethylidene]amino]oxymethyl-6,7-dihydroxy-2-quinolinecarboxylic acid, disodium salt A solution of the title H compound (1.5 g, 4.1 mmol) and the title J compound from Example 1 (0.69 g, 2.06 mmol) in dry dimethylformamide (70 mL) was stirred overnight at room temperature. The solvent was evaporated in vacuo and water (15 mL) added to the residue. The pH was adjusted to 6.3 by the addition of 2N-sodium hydroxide, some unsoluble material filtered off by suction and the filtrate subjected to MPLC on XAD using water as eluent. The product containing fractions were combined and further purified by MPLC on Organogen. A third MPLC on XAD was necessary to obtain the title compound of sufficient quality.

Yield: 83 mg impure. 25 mg H.I.=97.1%. 94 mg H.I.=95.3%. 75 mg H.I.=89.9%.

Total Yield: 194 mg (15%)
Melting point: dec. at 170° C.

What is claimed is:

1. Compounds having the formula

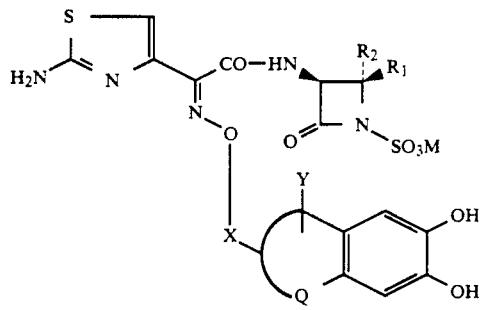

wherein $R_1$ and $R_2$ are the same or different and each is hydrogen, alkyl, alkenyl, alkynyl, cycloalkyl, phenyl, substituted phenyl or a 4, 5, 6 or 7-membered heterocycle, hereinafter referred to as $R_a$, or one of $R_1$ and $R_2$ is hydrogen and the other is azido, halomethyl, dihalomethyl, trihalomethyl, alkoxycarbonyl, phenylethyl, 2-phenylethenyl, 2-phenylethynyl, carboxyl, —CH$_2$X$_1$; wherein $X_1$ is azido, amino, hydroxy, carboxyl, alkoxycarbonyl, alkanoylamino, phenylcarbonylamino, (substituted phenyl) carbonylamino, alkylsulfonyloxy, phenylsulfonyloxy, (substituted phenyl) sulfonyloxy, phenyl, substituted phenyl, cyano

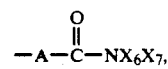

—S—X$_2$, or —O—X$_2$ wherein A, X$_2$, X$_6$ and X$_7$ are as hereinafter defined; —S—X$_2$ or —O—X$_2$; wherein X$_2$, is alkyl, substituted alkyl, phenyl, substituted phenyl, phenylalkyl, (substituted phenyl) alkyl, formyl, alkanoyl, substituted alkanoyl, phenylalkanoyl, substituted phenylalkanoyl, phenylcarbonyl, substituted phenylcarbonyl, heteroaryl, heteroarylalkyl, heteroarylalkanoyl or heteroarylcarbonyl, and in the case of when X$_1$ is —O—X$_2$ then X$_2$ can also be alkylideneamino, alkanoylamino, carboxyalkylideneamino, alkylsulphonylamino, alkoxycarbonyl or alkylsulphonylamino and $R_1$ and $R_2$ can be

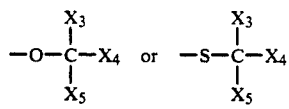

wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, substituted phenylcarbonyl, phenylalkylcarbonyl, substituted phenylalkylcarbonyl, carboxyl, alkoxycarbonyl, aminocarbonyl, substituted aminocarbonyl, or cyano; or

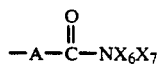

wherein A is $-CH=CH-$, $-(CH_2)_m-O-$, $-(CH_2)_m-NH-$, or $-CH_2-S-CH_2-$, m is 0, or an integer of 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ or $X_7$ when taken together with the nitrogen atom to which they are attached form a 4, 5, 6 or 7-membered heterocycle;

M is hydrogen, or a cation capable of forming a pharmaceutically acceptable salt;

Q completes a 6-membered aromatic or nonaromatic heterocyclic ring, optionally substituted with an oxo, having 1 to 2 heteroatoms independently selected from N and $NR_{12}$;

$R_{12}$ is hydrogen, lower alkyl, cycloalkyl or carboxyalkyl, or a salt thereof;

X is attached through an available carbon atom and is $(CH_2)_n$ wherein n is an integer of 1 to 4 or $CR_3R_4$ wherein $R_3$ and $R_4$ are the same or different and each is hydrogen, $CH_3$ or $C_2H_5$ or $R_3$ and $R_4$ taken together with the carbon atom to which they are attached form a 3, 4, 5, 6 or 7-membered cycloalkyl ring;

Y is attached through an available carbon atom and is hydrogen, amino, hydroxy, halogen, carboxamide or carboxyl; with the proviso that Q along with the attached benzo is not quinoxaline;

the term "substituted alkyl" refers to alkyl groups substituted with one or more azido, amino ($-NH_2$), halogen, hydroxy, carboxy, cyano, alkoxycarbonyl, aminocarbonyl, alkanoyloxy, alkoxy, phenyloxy, (substituted phenyl) oxy, $R_1$-oxy, mercapto, alkylthio, phenylthio, (substituted phenyl) thio, alkylsulfinyl, or alkylsulfonyl groups;

the term "substituted phenyl" refers to a phenyl group substituted with 1, 2 or 3 amino, halogen, hydroxyl, trifluoromethyl, alkyl (of 1 to 4 carbon atoms), alkoxy (of 1 to 4 carbon atoms), alkanoyloxy, aminocarbonyl, or carboxy groups;

the term "a 4, 5, 6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino, or alkyl wherein the alkyl group has 1 to 4 carbon atoms;

the term "substituted amino" refers to a group having the formula $-NX_8X_9$ wherein $X_8$ is hydrogen, alkyl, phenyl, substituted phenyl, phenylalkyl or (substituted phenyl) alkyl, and $X_9$ is alkyl, phenyl, substituted phenyl, phenylalkyl, (substituted phenyl) alkyl, hydroxy, cyano, alkoxy, phenylalkoxy or amino; and the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one, or more, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl groups, wherein the alkyl group has 1 to 4 carbon atoms.

2. A compound according to claim 1 wherein $R_1$ is hydrogen and $R_2$ is methyl.

3. A compound according to claim 1 wherein $R_1$ is methyl and $R_2$ is hydrogen.

4. A compound according to claim 1 wherein $R_1$ and $R_2$ are hydrogen.

5. A compound according to claim 1 wherein X is $(CH_2)_n$ and n is one.

6. A compound according to claim 1 wherein X is $(CH_2)_n$ and n is two.

7. A compound according to claim 1 wherein X is $(CH_2)_n$ and n is three.

8. A compound according to claim 1 wherein X is $(CH_2)_n$ and n is four.

9. A compound according to claim 5 wherein Q completes a quinolone ring wherein Y is hydrogen and $R_{12}$ is carboxyalkyl.

10. A compound according to claim 5 wherein Q completes a quinoline ring where Y is carboxy.

11. A compound according to claim 1 wherein X is $(CH_2)_n$; wherein n is an integer from one to four and $R_1$ or $R_2$ is methyl and the other is hydrogen.

12. A compound according to claim 1, [2R-[2α,3α(Z)]]-3-[[[1-(2-Amino-4-thiazolyl-2-[2-methyl-4-oxo-1-sulfo-3-azetidinyl)amino-2-oxoethylidene]amino]oxy]methyl]-6,7-dihydroxy-4-oxo-1(4H)-quinolineacetic acid, or a salt thereof.

13. A compound according to claim 1, [2R-[2α,3α(Z)]]-4-[[[[1-(2-Amino-4-thiazolyl-2-[(2-methyl-4-oxo-1-sulfo-3-azetidinyl)amino]-2-oxoethylidene]amino]oxy]methyl]-6,7-dihydroxy-2-quinolinecarboxylic acid, or a salt thereof.

14. A compound according to claim 1, [2R-[2α,3α(Z)]]-2-[[[[1-(2-Amino-4-thiazolyl-2-[(2-methyl-4-oxo-1-sulfo-3-azetidinyl)amino]-2-oxoethyldene]amino]oxy]methyl]-6,7-dihydroxy-4-quinolinecarboxylic acid, or a salt thereof.

* * * * *

UNITED STATES PATENT AND TRADEMARK OFFICE
CERTIFICATE OF CORRECTION

PATENT NO. : 5,250,691
DATED : October 5, 1993
INVENTOR(S) : Henner Straub et al.

It is certified that error appears in the above-identified patent and that said Letters Patent is hereby corrected as shown below:

Column 21, line 23, after the words "-CH=CH-,"

insert -- $-(CH_2)_m-,$ --.

Signed and Sealed this

Twenty-ninth Day of March, 1994

Attest:

BRUCE LEHMAN

*Attesting Officer*     *Commissioner of Patents and Trademarks*